(12) United States Patent
Lou et al.

(10) Patent No.: US 10,306,882 B2
(45) Date of Patent: Jun. 4, 2019

(54) BIOLOGICAL SAMPLE VITRIFICATION CARRIER AND USAGE THEREOF

(71) Applicants: Wei Lou, Shanghai (CN); Yanping Kuang, Shanghai (CN)

(72) Inventors: Wei Lou, Shanghai (CN); Yanping Kuang, Shanghai (CN)

(*) Notice: Subject to any disclaimer, the term of this patent is extended or adjusted under 35 U.S.C. 154(b) by 566 days.

(21) Appl. No.: 14/783,562

(22) PCT Filed: Apr. 9, 2014

(86) PCT No.: PCT/CN2014/074987
§ 371 (c)(1),
(2) Date: Oct. 9, 2015

(87) PCT Pub. No.: WO2014/166389
PCT Pub. Date: Oct. 16, 2014

(65) Prior Publication Data
US 2016/0057992 A1    Mar. 3, 2016

(30) Foreign Application Priority Data

Apr. 9, 2013  (CN) .......................... 2013 1 0121801

(51) Int. Cl.
*A01N 1/02*    (2006.01)
(52) U.S. Cl.
CPC .......... *A01N 1/0252* (2013.01); *A01N 1/0257* (2013.01); *A01N 1/0268* (2013.01)
(58) Field of Classification Search
CPC .......................... A01N 1/0252; A01N 1/0257; A01N 1/0268
(Continued)

(56) References Cited

U.S. PATENT DOCUMENTS

| 4,485,641 A | 12/1984 | Angelier et al. |
| 4,688,387 A * | 8/1987 | Conaway ............. A01N 1/0289 435/1.3 |

(Continued)

FOREIGN PATENT DOCUMENTS

| CN | 101200706 A | 6/2008 |
| CN | 201322489 Y | 10/2009 |

(Continued)

OTHER PUBLICATIONS

Cobo et al., Vitrification: an effective new approach to oocyte banking and preserving fertility in cancer patients. Clin Transl Oncol. May 2008;10(5):268-73.

(Continued)

*Primary Examiner* — Michael L Hobbs
*Assistant Examiner* — Liban M Hassan
(74) *Attorney, Agent, or Firm* — Wolf, Greenfield & Sacks, P.C.

(57) ABSTRACT

A biological sample vitrification carrier and a method for freezing a biological sample are provided. Specifically, the carrier comprises a main body and a sealing cap that form a sealed frozen sample placing region. Frozen liquid circulating in a liquid circulating channel in the main body contacts with an outer surface of the frozen sample placing region and cools a biological sample in the frozen sample placing region. The biological sample vitrification carrier and the method in the present invention have the advantages of safety, nontoxicity and high vitrification and rewarming operation efficiency and have wide application prospects in the field of biological sample freezing.

18 Claims, 4 Drawing Sheets

(58) Field of Classification Search
USPC .................................. 435/1.3, 284.1, 307.1
See application file for complete search history.

(56) References Cited

U.S. PATENT DOCUMENTS

| | | | | |
|---|---|---|---|---|
| 4,807,442 | A * | 2/1989 | Linner | B01D 8/00 118/50.1 |
| 6,615,592 | B2 * | 9/2003 | Prien | A01N 1/02 435/374 |
| 7,059,139 | B1 * | 6/2006 | Marsing | G01N 1/36 269/900 |
| 8,028,532 | B2 * | 10/2011 | Voute | A61J 1/165 62/66 |
| 2009/0019865 | A1 * | 1/2009 | Henderson | A01N 1/00 62/62 |
| 2010/0151570 | A1 * | 6/2010 | Kader | A01N 1/02 435/374 |

FOREIGN PATENT DOCUMENTS

| | | |
|---|---|---|
| CN | 101671627 A | 3/2010 |
| CN | 102204527 A | 10/2011 |
| CN | 102379278 A | 3/2012 |
| CN | 202311020 U | 7/2012 |
| CN | 103190393 A | 7/2013 |
| WO | WO 2009/105813 A1 | 9/2009 |
| WO | WO 2012/162384 A1 | 11/2012 |

OTHER PUBLICATIONS

Mie et al., Observation on the effects of closed pulled straw vitrification on naïve human embryos cryopreservation. Shandong Medical Journal. 2010;50(15):56-7.

Panagiotidis et al., Open versus closed vitrification of blastocysts from an oocyte-donation programme: a prospective randomized study. Reprod Biomed Online. May 2013;26(5):470-6. doi: 10.1016/j.rbmo.2013.01.016. Epub Feb. 9, 2013.

* cited by examiner

BIOLOGICAL SAMPLE VITRIFICATION CARRIER AND USAGE THEREOF

RELATED APPLICATIONS

This application is a national stage filing under 35 U.S.C. § 371 of International Application PCT/CN2014/74987 entitled "BIOLOGICAL SAMPLE VITRIFICATION CARRIER AND USAGE THEREOF" filed Apr. 9, 2014, which claims priority to CN Application No. 201310121801.9, filed Apr. 9, 2013, the entire disclosure of each of which is incorporated by reference in its entirety.

TECHNICAL FIELD

The present invention relates to the field of biological sample freezing device, specifically including providing a safe, effective and easily operated sealed freezing carrier for embryo(s) or egg cell(s) to be used in sterilized vitrification in the assisted reproductive technology field.

BACKGROUND ART

For artificial assisted reproductive technology, a common method for improving the success rate of in vitro fertilization and embryo transplantation is cryopreserving more embryos obtained by vitro fertilization or eggs obtained from female in the −196° C. liquid nitrogen for short-term or long-term selective embryo transplantation. The clinical significance of vitrification of biological sample is that the cryopreserved embryos or cells will stop development and be preserved for decades in coolant by a long-term preservation in a coolant such as liquid nitrogen, besides, upon rewarming the cryopreserved biological samples, one or more biologically live cells can be recovered.

When the materials are subjected to cryopreservation, the contact of material at room temperature with coolant at extremely low temperature (eg. liquid nitrogen) results in Leidenfrost effect, which causes the formation of vapor blanket to block conducting of heat, thereby decreasing the cooling rate of the desired freezing material. Generally, cryoprotectant is necessarily added to prevent the formation of ice crystals during freezing process of biological samples. However, cryoprotectant of high concentration is toxic to biological samples and will result in cells with low quality after recovery. Therefore, a vitrification technique for quick freezing is developed.

Currently, open-type vitrification carriers, such as open pulled straw, quartz capillary, Cryoloop, or Cryotip, etc., are generally used both domestically and abroad for increasing freezing rate. In 2005, Kuwayama proposed a new method, Cryotop method, that is, dipping the vitrification carrier loaded with a sample into the liquid nitrogen directly to increase cooling rate by minimizing the solution volumes. However, the biological sample was preserved in a non-sterilized condition, resulting the risk of cross contamination and the unpredictable direct toxic effect of liquid nitrogen on cells due to the direct contact of biological sample with liquid nitrogen (Covo A, Domingo J, Perez S, et al. Vitrification: an effective new approach to oocyte banking and preserving fertility in cancer patients [J]. Clin Transl Oncol, 2008, 10(5):268-273; Observation on the effects of closed pulled straw vitrification on naive human embryos cryopreservation, Shandong Medical Journal, Vol 50, N0. 15, 2010). The latest research further indicated that low molecular compounds in liquid nitrogen are toxic to biological samples (Y Panagiotidis, P Vanderzwalmen, Y Prapas, E kasapi, et, al Open versus closed vitrification of blastocysts from an oocyte-donation programme: a prospective randomized study. Reproductive BioMedicine Online, In Press, Uncorrected Proof, March 2013). Patent application No. 200710192245.9 disclosed a sealed vitrification device for preventing the exogenous pathogenic contamination to biological samples. However, although a sealed system for the isolation of coolant is obtained, the operation process of this type of cryopreservation carrier is still complicated since several steps such as thermoplastic sealing, etc., are needed.

Thus, there is an urgent need to develop a sealed freezing device for biological samples with high efficiency of vitrification, easy operation, safe and non-toxicity.

SUMMARY OF THE INVENTION

In the present invention, a sealed preservation device for biological samples with high efficiency of vitrification and easy operation is provided.

In the present invention, a vitrification carrier for biological sample is provided, and said carrier includes a body and a sealing cap, wherein the near end of the body and the bottom of the sealing cap are sealed to form a sealed placing area for a frozen sample, and a placing platform for a frozen sample is set in said placing area for a frozen sample, and a coolant circulation channel is set on said body, and a flow-through pore(s) corresponding to said coolant circulation channel is set on said sealing cap so as to enable the coolant in the circulation channel to contact with the outside surface of the placing area for a frozen sample when the biological sample is subjected to cryopreservation, thereby cooling the biological sample.

In another preferred embodiment, the coolant liquid flowing through the channel directly contacts with the outside surface of the placing platform for a frozen sample, thereby cooling the biological sample placed on the placing platform for a frozen sample.

In another preferred embodiment, when the biological sample is subjected to cryopreservation by said biological sample vitrification carrier, the coolant flowing through outside the vitrification carrier directly contacts with the outside surface of the placing platform for a frozen sample, thereby cooling the biological sample placed on the placing platform for a frozen sample.

In another preferred embodiment, there is sealing gasket between the near end of the body and the sealing cap.

In another preferred embodiment, said placing platform for a frozen sample is a flat surface with a size suitable for the sample; and (a) is located on the top of the near end of the body, or fixed on the top of the near end of the body; or (b) is located on the bottom of said sealing cap (especially on the inner bottom surface); or fixed on the bottom of said sealing cap.

In another preferred embodiment, the placing plateform for a frozen sample is on the same level with the top of the near end of the body; or said placing platform for a frozen sample is lower than the level of the top of near end of the body.

In another preferred embodiment, the height of the placing area for a frozen sample is 0.5-5 mm.

In another preferred embodiment, the forming mode of the placing platform includes molding, splicing or fastening the placing platform with the carrier body or the sealing cap.

In another preferred embodiment, said biological sample(s) includes: cell(s), tissue(s) or organ(s).

In another preferred embodiment, said cell(s) includes: egg cell(s) or embryo cell(s).

In another preferred embodiment, said body further includes a gripping part at the distal end of the body and an engaging part located between the near end and the distal end of the body for sealing and engaging with the sealing cap.

In another preferred embodiment, said channel has a distal opening(s) located on the gripping part and a side opening(s) located on the side wall of the body, and said distal opening(s) communicates with said side opening(s).

In another preferred embodiment, said distal opening(s) extends from the gripping part along the inner side of the body center to the near end of the body and forms the hollow body with opening(s) together with the placing platform for a frozen sample.

In another preferred embodiment, the side opening(s) on the side wall of the body locates between the placing area for a frozen sample and the engaging part, more preferably, the side opening(s) on the side wall of the body is adjacent to the placing area for a frozen sample.

In another preferred embodiment, the number of said openings on the side wall of the body is at least 2; more preferably, 4-6.

In another preferred embodiment, the surface of the engaging part has active fasteners for engaging with sealing cap.

In another preferred embodiment, the active fasteners include screw fasteners, socket fasteners, or buckle fasteners.

In another preferred embodiment, an information marking area for sample is set on the outside top surface or the side wall of the sealing cap.

In another preferred embodiment, different color is used for the sealing cap for identifying embryos in different growth phase, or cells or tissues of different types.

In another preferred embodiment, the diameter of the platform is 1-15 mm; more preferably, 3-12 mm; still more preferably, 5-10 mm; the most preferably, 6-8 mm; and/or
the thickness of the platform is 0.06-0.15 mm; more preferably; 0.07-0.12 mm; still more preferably, 0.08-0.10 mm; and/or
the height of the placing area for a biological sample is 0.5-5 mm; preferably; 1-4 mm; more preferably, 2-3 mm.

In another preferred embodiment, after a biological sample is placed, the freezing rate of the carrier is at least 10000-20000° C./min; more preferably, 30000-50000° C./min; still more preferably, 60000-100000° C./min.

In another preferred embodiment, materials of the body and the sealing cap can be identical or not, and selected from the group consisting of polymer material and metal; and/or
the material of the platform of the carrier is selected from the group consisting of polymer material and metal.

In another preferred embodiment, the polymer material comprises PE (polyethylene), HDPE (high density polyethylene), PP (polypropylene), or PET (polyethylene glycol terephthalate);

In another preferred embodiment, said metal comprises stainless steel or titanium alloy.

In another preferred embodiment, the polymer material or metal is medical polymer material or medical metal.

In another preferred embodiment, the diameter of the gripping part is 6-15 mm, and the diameter of the distal opening is 2-10 mm; and/or the size of the side opening is 1-3 mm×1-3 mm; and/or the size of the flow-through pore of the sealing cap is 2-5 mm×2-5 mm.

In another preferred embodiment, the coolant liquid circulation-channel is stair-step shaped or windowed cylinder shaped.

In another preferred embodiment, the side opening of the body is a circular aperture, an elliptical aperture, an irregularly-shaped aperture or a flat aperture.

In another preferred embodiment, the number of the side openings of the body is at least 2, more preferably 4-6; and the number of the flow-through pores of the sealing cap is at least 2, more preferably 4-6.

In the second aspect of the present, a method for sealed vitrification of biological sample(s) is provided, comprising the steps of:

a) providing a biological sample vitrification carrier according to the first aspect of the present invention, wherein said carrier includes a body and a sealing cap, and placing a biological sample(s) on the placing platform for a frozen sample of the biological sample vitrification carrier, so as to form a carrier body containing said biological sample(s);

b) engaging and tightening the carrier body containing said biological sample(s) obtained in step a) with the sealing cap, so as to form a sealed carrier containing the biological sample(s);

c) marking sample information on the marking area of the sealed carrier containing the biological sample(s) obtained in step b);

d) subjecting the sealed carrier marked with biological sample information obtained in step c) into a coolant for preservation.

In another preferred embodiment, the method for sealed vitrification of biological sample(s) further comprises: marking the sealed carrier containing biological sample(s); and/or marking the vitrification carrier followed by placing biological sample(s) into the carrier and then sealing the carrier, so as to obtain the marked sealing carrier containing the biological sample(s).

In the third aspect of the present invention, a combined device for biological sample cryopreservation is provided, and said combined device comprises i) one or more carriers according to the first aspect of the present invention; ii) liquid nitrogen; and iii) liquid nitrogen storage device.

In another preferred embodiment, the liquid nitrogen storage device has a support(s) actively connected with said liquid nitrogen storage device for containing said carrier(s).

In another preferred embodiment, the support(s) has a single-layer or multiple-layer structure, and each layer of said support(s) may contain 5-120; more preferably, 10-100; still more preferably, 20-80 of said carriers.

In another preferred embodiment, the size of the support(s) can be varied with the volume of the liquid nitrogen storage device.

The present invention further provides a use of the biological sample vitrification carrier according to the first aspect of the present invention for sealed cryopreservation of biological sample(s).

It should be understood that in the present invention, the technical features specifically described above and below (such as in the Examples) can be combined with each other, thereby constituting a new or preferred technical solution which needs not be described one by one.

Figure 1:
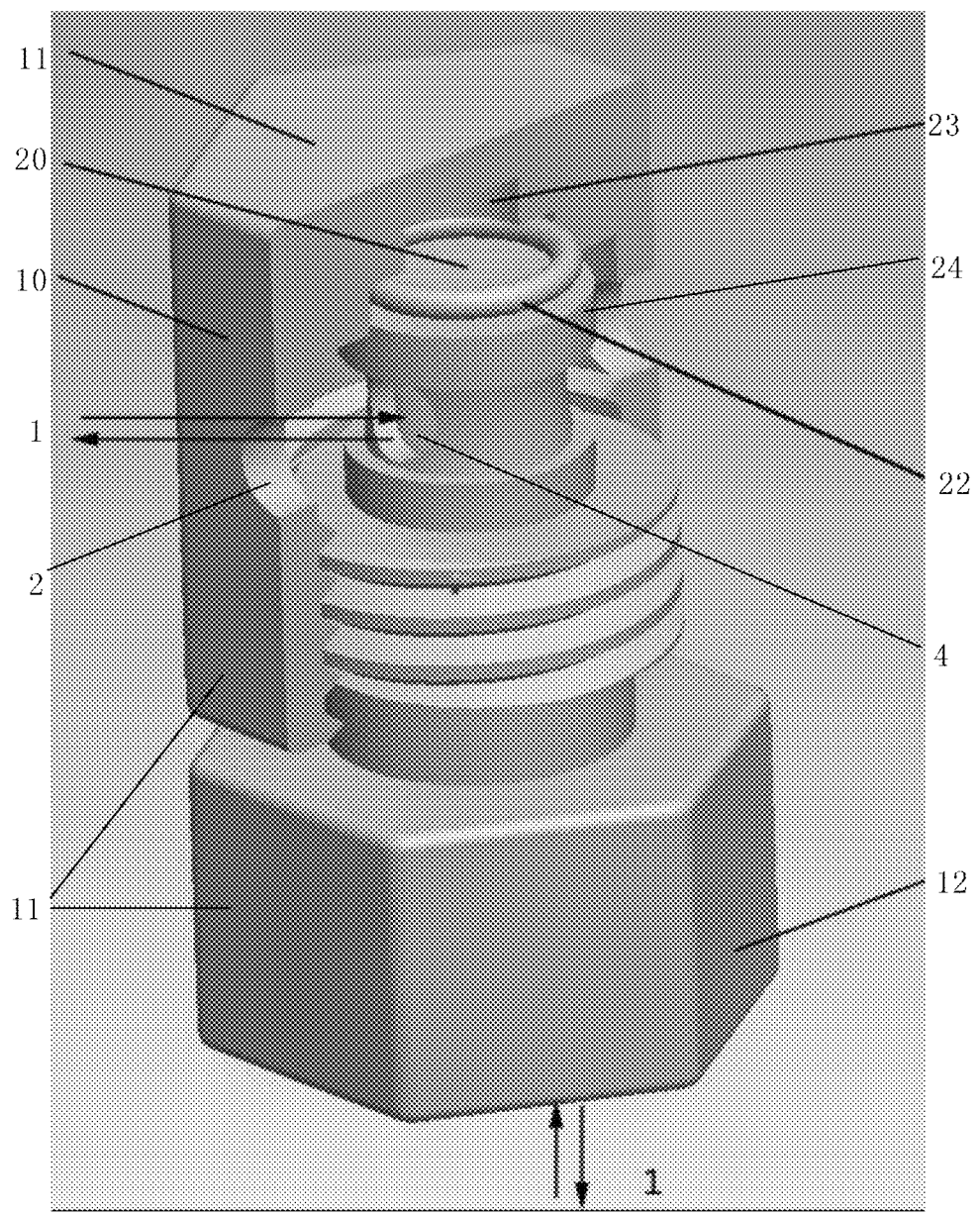
FIG. 1 shows the assembly diagram of the biological sample vitrification carrier 1 according to the present invention.

Wherein, parts of the carrier and the function thereof corresponding to the reference numbers are listed as follows:

1 coolant circulation channel; 2 flow-through pore; 4 side opening; 5 distal opening; 10 sealing cap; 11 marking area for the samples; 12 gripping part; 13 distal end; 20 placing platform for a frozen sample; 22 sealing gasket; 23 placing area for a frozen sample; 24 near end.

DETAILED EMBODIMENTS

Upon extensive and intensive research, the inventors firstly provided a carrier and a device for sealed cryopreservation of biological samples. It has been proven by the tests that the designed coolant circulation channel, coolant flow through pores and biological sample freezing platform of the carrier according to the present invention achieved sealed isolation of biological samples from coolant, and vitrification with high efficiency as well as a high survival rate of embryos upon recovery by an easy operation. The prevention is accomplished on this basis.

Placing Platform and Placing Area for a Frozen Sample(s)

In the present invention, a sealed placing area for a frozen sample is formed and sealed by the near end of the body and the bottom of the sealing cap, and a placing platform for a frozen sample is set on said placing area for a frozen sample.

Said platform can be fixed or connected to the top of the near end of the body and forms a hollow body structure with a sealed near end together with the near end of the body. Wherein, the plane of the platform can be at the same level as the top of the near end of the body, or lower than the level of the top of the near end of the body. Said platform can be fixed to the top of the near end of the body by various conventional fixing or connecting modes. Generally, it can be fixed to the body by compression molding, connected to the near end of the body by polymer binding agent, or buckle with the near end of the body by buckle fasteners. A preferred connecting mode is compression molding.

The platform can also be fixed or connected to the inner bottom surface of the sealing cap. When the platform is connected to the sealing cap, the body upends in the sealing cap and the near end of the body engages with the platform, thereby forming a sealed placing area for a frozen sample.

Typically, a sealing gasket is located along the perimeter of the placing area for a frozen sample for filling the gap between the near end of the body and the sealing cap so as to guarantee the seal of the placing area for a frozen sample and effectively prevent the contact of the biological sample with the coolant, thereby preventing the cross contamination and the harm of toxic matters such as unknown pathogens in the coolant to the biological sample.

The material for the placing platform for a frozen sample according to the present invention can be medical high molecular materials or metals which are non-toxic and tolerant to the temperature variation due to shock cooling and shock heating. Generally, the material used in the placing platform for a frozen sample according to the present invention includes PE, HDPE, PET, PP, medical stainless steel or medical titanium alloy.

The freezing sample placing platform is characterized that the diameter of the platform is 1-15 mm; more preferably, 3-12 mm; still more preferably, 5-10 mm; the most preferably, 6-8 mm; and/or the thickness of the carrier platform is 0.06-0.15 mm; more preferably, 0.07-0.12 mm; still more preferably, 0.08-0.10 mm.

Furthermore, the size of the biological sample vitrification carrier according to the present invention can be varied with the particular size of desired freezing biological sample and the removal of the extra coolant. Typically, the diameter of the platform of the vitrification carrier can be 1-15 mm and the height thereof can be 0.5-5 mm.

Coolant Circulation Channel

The coolant circulation channel used in the present invention comprises the following parts:

(a) distal opening(s) located at the distal end of the body;

(b) side opening(s) located at the near end of the body;

(c) flow-through pore(s) on the side wall of the sealing cap and corresponding to the side opening(s) on the near end of the body.

Wherein, the distal opening(s) and the side opening(s) communicate with each other through the body center and correspond to the flow-through pore(s) on the side wall of the sealing cap. The side opening(s) locates at the near end of the body; and more preferably, said side opening(s) is adjacent to the placing platform for a frozen sample.

Generally, there are at least 2, more preferably 4 or more side openings and flow-through pores, respectively.

According to the present invention, when the sealing cap is sealed with the body and then the carrier is placed into coolant liquid, the coolant liquid circulates along the distal opening(s)—the side opening(s)—flow-through pore(s) of the coolant circulation channel. Thus, the circulation process of the coolant allows the platform surface of the biological sample carrier to be pre-cooled. Leidenfrost Effect is decreased since the carrier platform is thin enough, thereby allowing the tissue sample(s) on the placing platform to be cooled rapidly.

According to the present invention, the diameter of the side opening(s) is 1-3 mm or the side opening(s) is elliptical transverse aperture with a size of 2×3 mm, and the flow-through pore(s) of the sealing cap is (a) elliptical transverse aperture(s) with a size of 2-5 mm×2-5 mm.

The stereo shape of the distal opening, the side opening or the flow-through pore of the body used in the present invention is not specifically limited. It can be any matching shape proper for coolant circulation. Generally, the stereo shape of openings or the flow through pores is stair-step shaped or windowed cylinder shaped.

A Method for Fast Freezing Biological Samples

The method for fast freezing biological samples according to the present invention comprises the following steps:

a) providing a biological sample vitrification carrier according to claim 1, wherein said carrier includes a body and a sealing cap, and placing a biological sample(s) on the placing platform for a frozen sample of the biological sample vitrification carrier, so as to form a carrier body containing said biological sample(s);

b) engaging and tightening the carrier body containing said biological sample(s) obtained in step a) with the sealing cap, so as to form a sealed carrier containing the biological sample(s);

c) marking sample information on the marking area of the sealed carrier containing the biological sample(s) obtained in step b);

d) subjecting the sealed carrier marked with biological sample information obtained in step c) into a coolant for preservation.

Generally, the method for sealed vitrification of biological sample(s) further comprises: marking the sealed carrier containing biological sample(s); and/or marking the vitrification carrier followed by placing biological sample(s) into the carrier and then sealing the carrier, so as to obtain the marked sealing carrier containing the biological sample(s).

A freezing rate of 20000° C./min, preferably 40000-100000° C./min can be achieved by using the vitrification carrier and the method for fast freezing biological samples according to the present invention, and different freezing rates and vitrification effects of biological samples can be varied with different materials or sizes of the used carrier platform.

Beside, when subjected to experiments, diagnosis or treatments, the carrier according to the present invention should be sterilized before using and an aseptic condition should be maintained during the procedure.

Materials and Appearance

The materials used for preparing the biological sample vitrification carrier according to the present invention are non-toxic, sterilized polymer materials or metals which can be tolerant to the temperature variation due to shock cooling and shock heating.

In another preferred embodiment, the polymer material comprises PE (polyethylene), HDPE (high density polyethylene), PP (polypropylene), or PET (polyethylene glycol terephthalate).

In another preferred embodiment, said metal comprises stainless steel or titanium alloy.

In another preferred embodiment, the polymer material or metal is medical polymer material or medical metal.

According to the present invention, the body engages and is sealed with the sealing cap by various active fasteners such as buckle fasteners or screw fasteners. Generally, sealing effects can be achieved through buckle or screw fasteners by various conventional method, such as by adding sealing gasket which can tolerant to the temperature variation due to shock cooling and shock heating, modifying the shape or angle of the screw, so as to ensure the sealing and self-locking of the sealed device during shock cooling or shock heating.

The appearance of the body and the sealing cap according to the present invention is not specifically limited. Any column-shaped appearance matching each other can be used, such as cylinder shape or hexagon prism shape, so as to allow the operator to grip and ensure the carrier stabile when the biological samples such as embryos or eggs are placed. Furthermore, different color can be used for the body and the sealing cap for identifying different freezing biological samples, cells or tissues, etc.

The Advantage of the Present Invention:

1. Biological samples can be sealed and preserved safely and non-toxically: the carrier of the present invention and the use thereof are safe and non-contaminative, therefore biological samples can be isolated from coolant liquid and sealed preservation, and the potential toxic risks of coolant liquid to biological samples can be reduced.

2. High efficient vitrification can be achieved by fast freezing rate: a freezing rate of 10000-100000° C./min can be achieved by using the carrier of the present invention and use thereof, and different freezing rates and biological sample vitrification effects varies with different materials or sizes of the carrier platform, thereby achieving fast vitrification as well as avoiding the destructive effect of ice crystal on biological samples during freezing procedure.

3. Easy to operate: sealing method such as screw fastening or socket or buckle fastening is used for the present invention. During operation, the samples are placed on the platform, then the sealing cap can be tightened and the samples are subjected to liquid nitrogen for storage, instead of a complicated procedures such as thermoplastic sealing.

4. Safe and efficient: The removal procedure is as convenient as loading upon recovering the samples due to the special structure and easy operation of the present carrier. Loss of the samples rarely happens after recovery.

EXAMPLE 1

Figure 3:
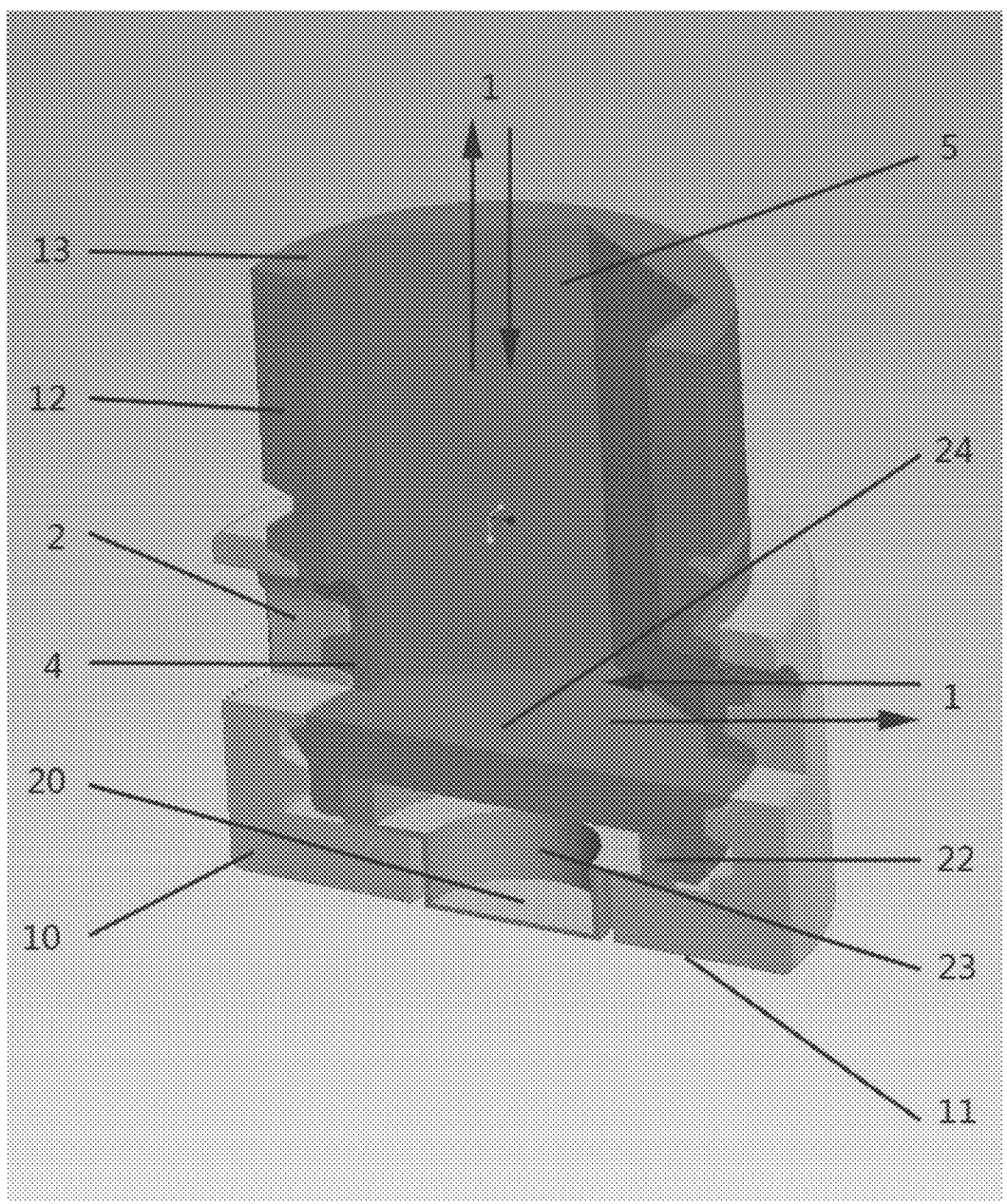
FIG. 3 shows the assembly diagram of the biological sample vitrification carrier 3 according to the present invention.
Figure 4:
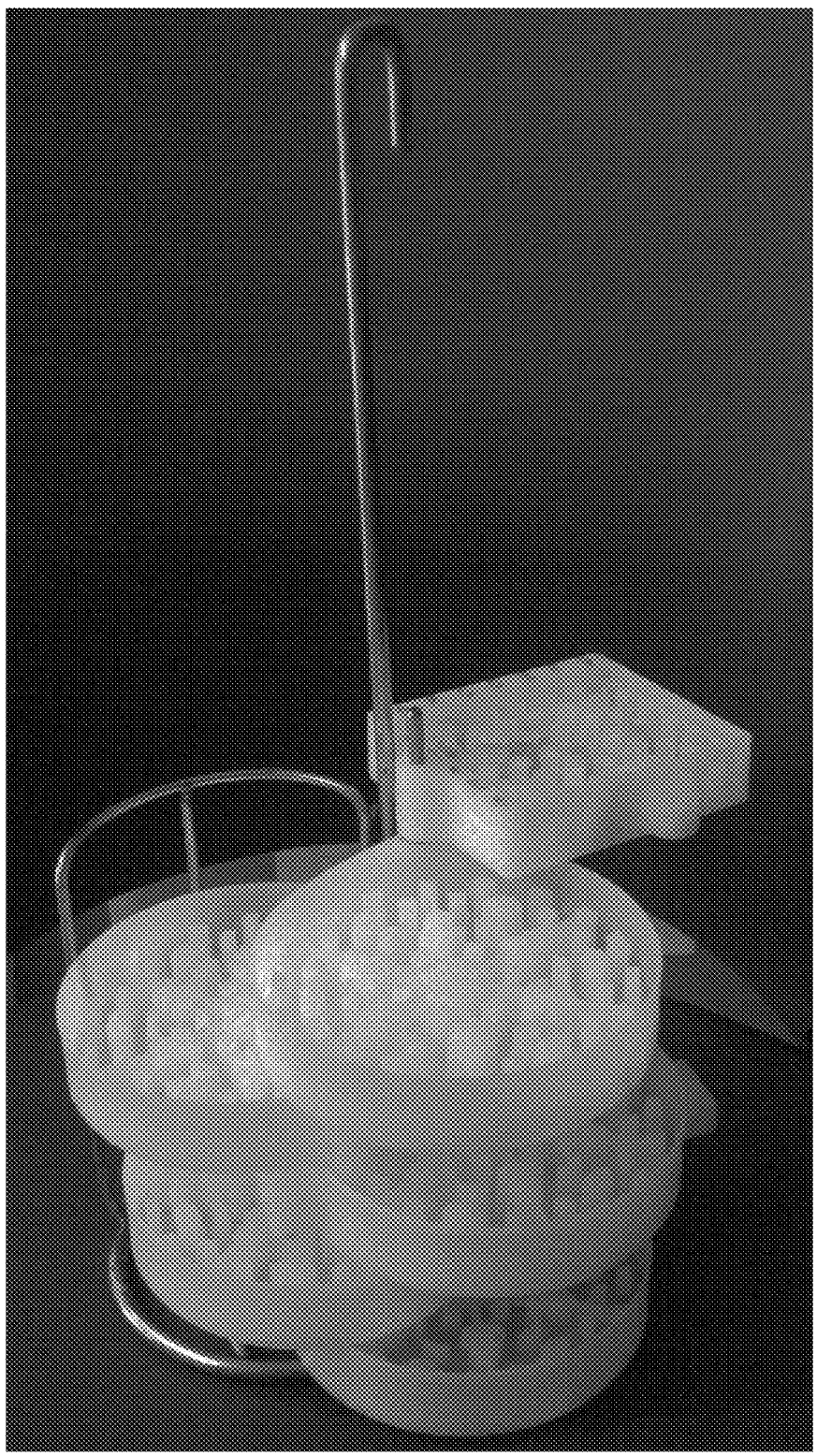
FIG. 4 shows the photo of the support in the combined device for biological sample cryopreservation.

Test for Sealing Performance 50 sets of sealed vitrification carrier 1 (FIG. 1) and carrier 3 (FIG. 3) are taken respectively, sterilized and placed into liquid nitrogen for 1 day, 1 week, 30 days, 60 days and 90 days. Then, the carriers were taken out from the liquid nitrogen and placed into 37° C. water immediately for 10 mins. The carriers were then placed on filter paper for a few seconds. The sealing caps were removed and clean filter paper was used for cleaning the placing platform. The filter paper was observed under microscope for water stain. Results are shown in Table 1:

TABLE 1

| Items for sealing | | Days in liquid nigtrogen (day) | | | | |
|---|---|---|---|---|---|---|
| | Performance | 1 | 7 | 30 | 60 | 90 |
| Carrier 1 | The number of tested sets | 10 | 10 | 10 | 10 | 10 |
| | Results of water stain test | None | None | None | None | None |
| Carrier 3 | The number of tested sets | 10 | 10 | 10 | 10 | 10 |
| | Results of water stain test | None | None | None | None | None |

The results showed that the carrier can be 100% sealed.

EXAMPLE 2

Survival Rate of Eggs or Embryos

1. Test Subject

Experimental animals are 80 female (9-week-old, 29-33 g/mice) Kunming Mice of clean grade and 20 male (9-week-old, 38-45 g/mice) mice (purchased from Shanghai Institute of Biological Products). The animals were exposed to 12-hour-circle of light and darkness.

2. Experimental Method:

1) Oocytes collection: sexually matured female Kunming mice were treated with ovulation induction and then sacrificed by cervical dislocation. The oviduct was separated, and oocytes with complete zona pellucida and good intracellular substance refractivity were collected (no damage in zona pellucida or cell membrane, clear periviteline space, no cell plasma leaking or egg cell atrophy, normal size, and good intracellular substance refractivity).

2) Sperm collection: seminal fluid was obtained by sacrificing healthy male mice through breaking the spine on the day of fertilization.

3) In vitro fertilization: the seminal fluid was co-incubated with eggs at a concentration of $2\times10^6$/ml for 5 hours and then recovered. The formation of bipronuclear cells was observed after the eggs were cultured in 37° C. and 5% $CO_2$ incubator for 24 hours.

Figure 2:
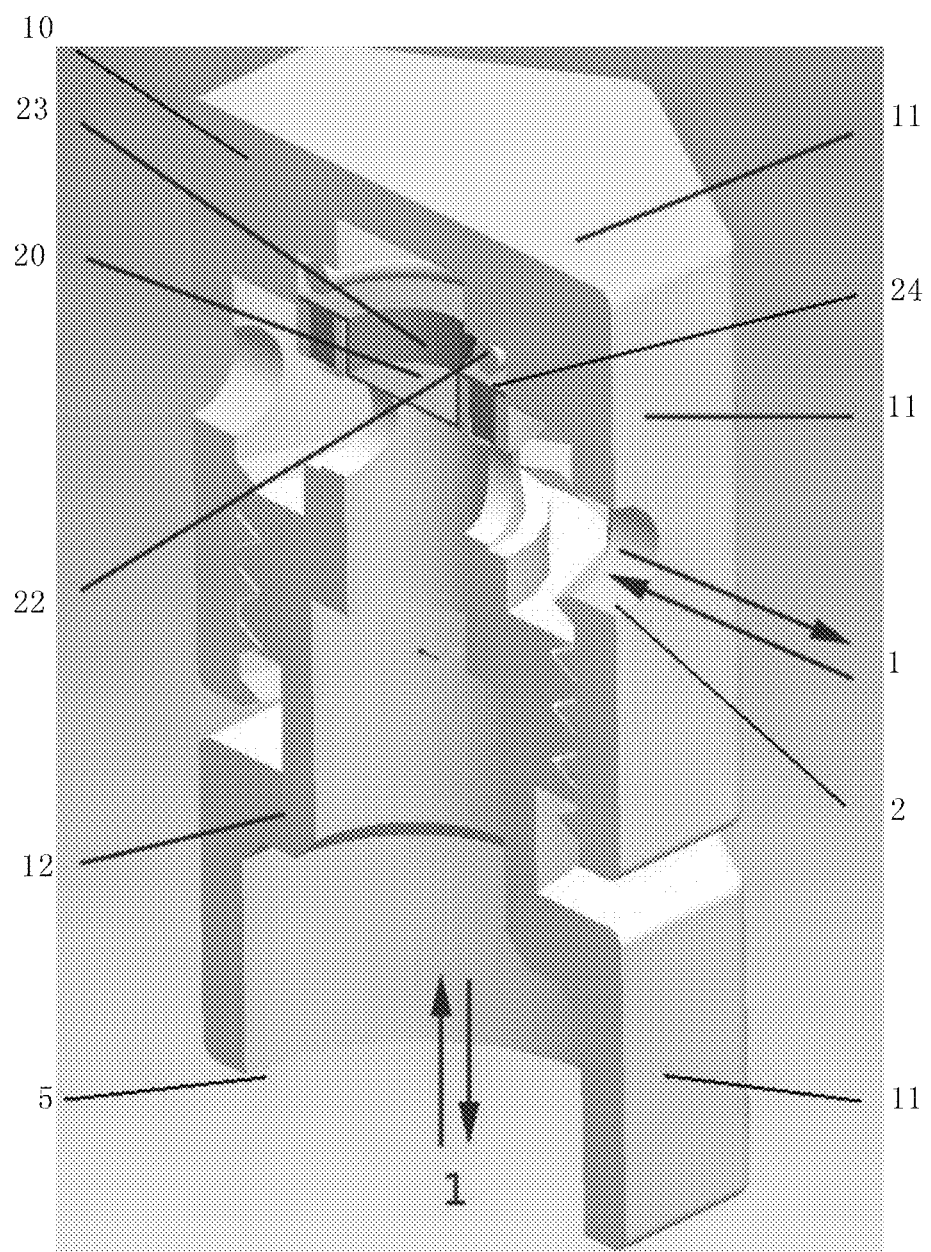
FIG. 2 shows the assembly diagram of the biological sample vitrification carrier 2 according to the present invention.

4) Vitrification carrier: 80 sets of sterilized vitrification carrier 1 (FIG. 1), 2 (FIG. 2) and 3 (FIG. 3) according to the present invention were respectively taken and assembled, and then qualified pronucleus embryos were selected and subjected to liquid nitrogen for vitrification for 3 days. Then, the carriers were taken out, and the embryos were rewarmed, cultured and observed for the embryo division.

Wherein, the number of 2-cell-embryos refers to the number of survival embryos which were divided into 2 cells obtained by 1 day cell culture; the number of 4-cell-embryos refers to the number of survival embryos which were divided into 4 cells obtained by 48-hour cell culture; the number of blastocysts refers to the number of the cells in blastula stage obtained by 96-hour cell culture.

3. The results of the mice pronucleus embryos vitrification by using the carrier according to the present invention are shown in table 2:

TABLE 2

| Vitrification carrier | The number of Pronucleus embryo | (%) 2-cell rate | (%) 4-cell rate | (%) blastocyst rate |
|---|---|---|---|---|
| Carrier 1 | 80 | 75.00 (60/80) | 65.00 (39/60) | 51.67 (31/60) |
| Carrier 2 | 80 | 81.25 (65/80) | 72.30 (47/65) | 66.15 (43/65) |
| Carrier 3 | 80 | 83.75 (67/80) | 76.12 (51/67) | 73.13 (49/67) |

Note:
2-cell rate = the number of/the number of pronucleus embryos;
4-cell rate = the number of 4-cell-embryos/the number of 2-cell-embryos;
blastocyst rate = the number of blastocysts/the number of 2-cell-embryos.

5. Conclusion

In this field, the blastocyst rate of a biological sample (embryo) from vitrification by using open or sealed vitrification carrier is about 50%-70%. According to the results of the above examples, the blastocyst rates of the embryos from vitrification by using the carriers according to the present invention are 51.67%, 66.15% and 73.13% respectively. The results are similar to, or even better than the blastocyst rates by using other devices or methods in this field. Moreover, the carrier according to the present invention has the advantages of easy operation and high safety. Thus, it can substitute the conventional devices and methods and is suitable for extensive use.

All references mentioned in the present invention are incorporated herein by reference, as each of them is individually cited herein by reference. Further, it should be understood that, after reading the above contents, the skilled person can make various modifications or changes to the present invention. All these equivalents also fall into the scope defined by the appending claims of the present application.

The invention claimed is:

1. A vitrification carrier for a biological sample, wherein said vitrification carrier includes a body and a sealing cap, the body having a first end and a second end, and wherein the first end of the body and a bottom of the sealing cap are sealed together to form a sealed placing area for the biological sample, and wherein a placing platform for the biological sample is included in said sealed placing area for the biological sample, and wherein a coolant circulation channel is included on said body, and wherein a flow-through pore is included on said sealing cap, wherein the coolant circulation channel and the flow-through pore are configured to enable a coolant in the coolant circulation channel to contact with an outside surface of the sealed placing area for the biological sample when the biological sample is subjected to cryopreservation, thereby cooling the biological sample, and wherein fluid communication between the coolant circulation channel and an inside volume of the sealed placing area is closed such that the biological sample in the sealed placing area is isolated from the coolant in the coolant circulation channel, and wherein the second end is a distal end of the body, said coolant circulation channel has a distal opening located on the distal end of the body and a side opening located on a side wall of the body, and said distal opening communicates with said side opening.

2. The vitrification carrier according to claim 1, wherein said placing platform for the biological sample is a flat surface with a size configured for placing the biological sample; and
   (a) is located on a top of the first end of the body, or fixed on the top of the first end of the body; or
   (b) is located on the bottom of said sealing cap; or fixed on the bottom of said sealing cap.

3. The vitrification carrier according to claim 1, wherein the second end is a distal end of the body, and an engaging part located between the first end and the distal end of the body for sealing and engaging with the sealing cap, wherein a surface of the engaging part has an active fastener for engaging with the sealing cap, and wherein the active fastener is selected from the group consisting of a screw fastener, a socket fastener, and a buckle fastener.

4. The vitrification carrier according to claim 3, wherein the active fastener is a screw fastener.

5. The vitrification carrier according to claim 1, wherein
   a diameter of the placing platform is 1-15 mm; and/or
   a thickness of the placing platform is 0.06-0.15 mm; and/or
   a height of the sealed placing area for the biological sample is 0.5-5 mm.

6. The vitrification carrier according to claim 1, wherein a freezing rate of the biological sample in the vitrification carrier is at least 10000-20000° C./min.

7. The vitrification carrier according to claim 1, wherein the body, the placing platform and the sealing cap comprise identical material or different materials.

8. The vitrification carrier according to claim 1, wherein a diameter of the distal end of the body is 6-15 mm.

9. The vitrification carrier according to claim 1, wherein the body comprises at least two side openings and the sealing cap comprises at least two flow-through pores.

10. A method for sealed vitrification of a biological sample, comprising the steps of:
- a) providing a vitrification carrier according to claim 1, and placing a biological sample on the placing platform of the vitrification carrier, so as to form a carrier body containing said biological sample;
- b) engaging and tightening the carrier body containing said biological sample obtained in step a) with the sealing cap, so as to form a sealed carrier containing the biological sample;
- c) marking sample information on a marking area of the sealed carrier containing the biological sample obtained in step b); and
- d) subjecting the sealed carrier marked with biological sample information obtained in step c) into a coolant for preservation.

11. A combined device for biological sample cryopreservation, wherein said combined device comprises i) one or more vitrification carriers according to claim 1; ii) liquid nitrogen; and iii) a liquid nitrogen storage device.

12. The vitrification carrier according to claim 3, wherein said coolant circulation channel has a distal opening located at the distal end and a side opening located on a side wall of the body, and said distal opening communicates with said side opening.

13. The vitrification carrier according to claim 3, wherein a surface of the engaging part has active fasteners for engaging with the sealing cap.

14. The vitrification carrier according to claim 2, wherein the bottom of said sealing cap is an inner bottom surface of the sealing cap.

15. The vitrification carrier according to claim 7, wherein the identical material is a polymer or a metal and the different materials are a polymer and a metal.

16. The vitrification carrier according to claim 1, wherein a diameter of the distal opening is 2-10 mm.

17. The vitrification carrier according to claim 1, wherein a size of the side opening is 1-3 mm×1-3 mm.

18. The vitrification carrier according to claim 1, wherein a size of the flow-through pore of the sealing cap is 2-5 mm×2-5 mm.

* * * * *